(12) United States Patent
Harris

(10) Patent No.: US 6,818,597 B2
(45) Date of Patent: Nov. 16, 2004

(54) SUSPENSIONS OF WATER SOLUBLE POLYMERS IN SURFACTANT FREE NON-AQUEOUS SOLVENTS

(75) Inventor: William Franklin Harris, Friendswood, TX (US)

(73) Assignee: Benchmark Research & Technology, Inc., Midland, TX (US)

( * ) Notice: Subject to any disclaimer, the term of this patent is extended or adjusted under 35 U.S.C. 154(b) by 187 days.

(21) Appl. No.: 09/771,226

(22) Filed: Jan. 26, 2001

(65) Prior Publication Data

US 2002/0019318 A1 Feb. 14, 2002

Related U.S. Application Data

(60) Provisional application No. 60/198,922, filed on Apr. 21, 2000.

(51) Int. Cl.[7] ............................ C09K 7/06; B01D 21/01
(52) U.S. Cl. ...................... 507/136; 507/138; 507/110; 507/111; 507/112; 507/113; 507/114; 507/115; 507/119; 507/124; 507/209; 507/211; 507/212; 507/213; 507/214; 507/215; 507/216; 507/217; 507/224; 507/230; 507/261; 507/265; 507/925; 516/104; 516/105; 516/106; 516/107; 524/275; 524/276
(58) Field of Search ........................ 524/275, 276; 516/104–107; 507/110–115, 119, 124, 136, 138, 209, 211–217, 224, 230, 261, 265, 925

(56) References Cited

U.S. PATENT DOCUMENTS

| | | | | |
|---|---|---|---|---|
| 3,780,170 A | * | 12/1973 | Goodhart | 424/495 |
| 4,176,107 A | | 11/1979 | Buckman et al. | 260/29.6 E |
| 4,336,145 A | | 6/1982 | Briscoe | 252/8.55 R |
| 4,425,241 A | | 1/1984 | Swanson | 252/8.5 C |
| 4,453,979 A | | 6/1984 | DeMasi et al. | 106/188 |
| 4,566,977 A | | 1/1986 | Hatfield | 252/8.5 C |
| 4,754,027 A | | 6/1988 | Applegren | 536/114 |
| 4,799,962 A | | 1/1989 | Ahmed | 106/188 |
| 4,895,567 A | * | 1/1990 | Colon et al. | 524/275 |
| 5,080,717 A | | 1/1992 | Young | 106/197.1 |
| 5,091,448 A | | 2/1992 | Hostettler et al. | 524/45 |
| 5,246,490 A | | 9/1993 | Kehoe et al. | 106/189 |
| 5,362,312 A | | 11/1994 | Skaggs et al. | 106/189 |
| 5,487,777 A | | 1/1996 | Lundan et al. | 106/188 |
| 5,710,108 A | * | 1/1998 | McNally et al. | 507/138 |
| 5,932,193 A | | 8/1999 | Lopez et al. | 424/52 |
| 5,969,012 A | | 10/1999 | Harris, Jr. | 524/55 |
| 5,985,801 A | | 11/1999 | Hoff | |
| 6,187,719 B1 | * | 2/2001 | Dino et al. | 507/138 |

FOREIGN PATENT DOCUMENTS

GB          1363182          5/1972

\* cited by examiner

Primary Examiner—Philip C. Tucker
(74) Attorney, Agent, or Firm—Christopher L. Makay

(57) ABSTRACT

Liquid water soluble polymer suspensions in non-aqueous solvents are extremely stable over long periods of time with minimum separation of the solvent and no hard packing of the dispersed water soluble polymer. The suspensions enable a user to rapidly add the suspension to water, being mixed at low speeds, without the formation of lumps or fisheyes and without generating fugitive dust in the process. The suspensions are environmentally safe and biodegradable. Unlike many other liquid polymer suspensions, the suspensions exhibit minimal oil or grease upon dilution. They contain no surfactants that can add to the oil and grease determination. The suspensions and the fluids produced by diluting the fluids to a working concentration of the water soluble polymer exhibit low toxicity to marine organisms and to humans. The suspensions can be manufactured from ingredients suitable for use in personal care applications such as cosmetics, shampoos and the like. The suspensions can be manufactured using ingredients suitable for use in indirect contact with food. The suspensions are also pourable at low temperatures. The suspensions are also suitable for use in the formulation of fluids suitable for use in hydraulic fracturing and other well applications.

98 Claims, No Drawings

SUSPENSIONS OF WATER SOLUBLE POLYMERS IN SURFACTANT FREE NON-AQUEOUS SOLVENTS

This application claims benefit of provisional application 60/198,922 filed on Apr. 21, 2000.

BACKGROUND OF THE INVENTION

1. Field of the Invention

The present invention relates to stable non-aqueous suspensions of water-soluble polymers and, more particularly, but not by way of limitation to suspensions characterized by a medium of low molecular weight polyethylene glycol and a stabilizer of hydrogenated castor wax or oil.

2. Description of the Related Art

Hydrophilic polymers or gums are widely used in industry. They are used to thicken, suspend or stabilize aqueous systems. These gums can produce gels or act as emulsion stabilizers, flocculants, binders, film formers, lubricants and friction reducers. In many of these applications, the polymers are used to adjust and control the Theological properties of the aqueous system to which they are being added.

For commercial and industrial applications, rapid addition of these gums to water is highly desirable. Doing so, however, often results in the formation of lumps ("fisheyes") of unhydrated polymer. These lumps are gel-like agglomerates of many individual polymer particles. They are frequently wet on the outside but dry on the inside, and form as a result of the polymer beginning to hydrate before the individual polymer particles are dispersed. Once the outer layer of polymer is hydrated, the lump or fisheye often cannot be dispersed even with vigorous mixing. Removal of these lumps results in significant losses of time, material, and polymer efficiency.

Many treatments and procedures are carried out in industry utilizing high viscosity fluids to accomplish a number of purposes. For example, in the oil industry, high viscosity aqueous well treating fluids are utilized in treatments to increase the recovery of hydrocarbons from subterranean formations such as by creating fractures in the formations, acidizing the formations, etc. High viscosity aqueous fluids are also commonly utilized in well completion procedures. For example, during the completion of a well, a high viscosity aqueous completion fluid having a high density is introduced into the well to maintain hydrostatic pressure on the formation which is higher than the pressure exerted by fluids contained in the formation thereby preventing the formation fluids from flowing into the wellbore.

Heretofore, in preparing high viscosity treating fluids it has been necessary to utilize a number of dry additives that are mixed with water or other aqueous fluid at the job site. A number of disadvantages are inherent in such mixing procedures, particularly when large volumes of treating fluids are prepared. For example, special mixing equipment for mixing the dry additives with water is required and problems such as chemical dusting, uneven mixing, lumping of gels while mixing and extended preparation and mixing time are involved. In addition, the mixing and physical handling of large quantities of dry chemicals require a great deal of manpower, and where continuous mixing is required, the accurate and efficient handling of chemicals such as salts, viscosifying agents, crosslinkers, gel breakers, fluid loss control additives, and surfactants is extremely difficult.

These lumps are particularly problematic in the oil and gas industry where water soluble polymers are used downhole during drilling, workover, completion, stimulation and reservoir flooding operations. These unhydrated lumps, substantially inert to enzymes, chemical breakers and acids, cause a variety of problems including plugging of the well and permeability impairment of the oil-bearing strata. In addition, when polymers are used they are typically added to water in a dilute solution. During this operation fugitive dust is often generated. This dust has a number of potential detrimental effects. Workers preparing the solution can inhale the dust. Some of the polymers that can be suspended in a non-toxic solvent produce dust when handled in a powdered form that may produce a respiratory allergenic response and/or irritation to some individuals. Dust can also drift to areas where it is not intended.

To avoid lump or dust formation and its associated problems, the polymers can be added to the aqueous systems as liquid slurries or suspensions. A number of methods for accomplishing this, and the compositions prepared thereby, are described in the prior art. Unlike the present invention, they often use oil carriers (e.g., mineral, isoparaffin or diesel) to suspend and deliver the polymers to the aqueous systems. Recent regulations by the Environmental Protection Agency limit the amount of oil or grease that can be used in offshore oilfield applications for well treatment fluids. The National Pollutant Discharge Elimination System (NPDES) General Permit issued on Apr. 19, 1999 (Federal Register Vol. 64 No. 74) limits the oil and grease to a daily maximum concentration of 42 mg/l and a monthly average of 29 mg/l when the slurry is diluted to the intended use level with fresh or salt water. Unlike the liquid slurries that contain diesel fuel or other hydrocarbon solvents the suspensions of the present invention contain minimal detectable oil or grease when diluted to the concentration appropriate for use as a well treatment fluid.

U.S. Pat. No. 5,091,448 discloses a suspending medium for a water-soluble polymer. This patent utilizes isopariffin oils as the solvent for a suspension where a styrene/isoprene copolymer is used as the suspension agent. Upon dilution to the intended use concentration in fresh or salt water for a well treatment fluid, the dilution will contain a much higher concentration of oil and grease than is permitted by the above regulations. Furthermore the styrene/isoprene copolymer that is used to stabilize the suspension is insoluble in water miscible solvents such as the polyalkylene glycols of the present invention.

In addition to the oil carrier fluid, many hydrocarbon solvent-based slurries usually contain clay or clay like particulates that act to viscosify and stabilize the non-aqueous slurry. The disadvantages of these carrier systems are that attempts to eliminate the oil, often an undesirable component, result in the substitution of oil by toxic glycol ether. The clay component itself is also often times an undesirable component. This is particularly true in oil and gas field applications where incorporation of the clay into the slurries, which is necessary to keep the polymer in solution, impairs the permeability of the oil or gas bearing strata. This is not unlike the very problem caused by the formation of fisheyes that the oil slurry is supposed to eliminate.

U.S. Pat. No. 4,176,107 discloses liquid polymer compositions and to methods of preparing these compositions which comprise a high molecular weight water-soluble vinyl addition polymer, water, one or more surfactants, and a water-soluble polyalkylene glycol, or water-soluble ethoxylated alcohol, alkylphenol or fatty acid. U.S. Pat. No. 4,453,979 describes the use of water with a high molecular weight blend of water and polyethylene glycol to disperse hydrophilic gums. European Publication 58 017 describes the use of a water and clay based drilling fluid that contains high molecular weight polyethylene glycol. Polyethylene glycols ranging in molecular weight from 1000 to 10,000,000, which are solid at room temperature, are mentioned. U.S. Pat. No. 4,799,962 discloses a particulate water-soluble polymer dispersed in a liquid medium comprised of low molecular weight polyethylene glycol, water, and high molecular weight polyethylene glycol in amounts sufficient to impart stability to the dispersion. U.S. Pat. No. 5,362,312 discloses a carrier for water-soluble polymers that includes polyethylene glycol; one or more viscosified polyol fluid components; and one or more viscosifying polysaccharides. U.S. Pat. No. 5,932,193 discloses a carrier for water-soluble polymers that include polyethylene glycol and a hydrated thickening silica to aid in the stability of fluidized polymer slurry.

U.K. Patent No. 1,363,182 discloses a transparent or translucent gel toothpaste composition comprising polyethylene glycol having molecular weight below 700, and hydrated silica gel polishing agent having a specific surface area below 600 $m^2$/g. The composition may be thickened with carboxymethyl cellulose. Hydrated thickening silica is incorporated in the fluidized polymer suspensions of this invention to serve as a suspending agent for the dispersed water-soluble polymer. Hydrated thickening silicas are synthetic silicas comprising fumed silicas, amorphous precipitated silicas, and gel silica. The preferred hydrated thickening silicas, also known as thickening silicas, are colloidal gel silicas. More preferred ones are Aerosil®200 silica, available from Degussa AG, Frankfurt, Germany.

U.S. Pat. No. 5,969,012 discloses a non-aqueous suspension of water soluble polymers comprising one or more water soluble polymers; a polyalkylene glycol and a slurry stabilizer comprising an amine phosphate ester salt. This composition has application including oil recovery, and the paper and textile industries. This amine phosphate ester is an emulsifying surfactant that must be reacted for use in the suspension. Furthermore, the surfactant can emulsify oil and grease from oil-bearing formations, which can lead to excessive oil and grease in the produced water in excess of the limits imposed by the NPDES General Permit.

The foregoing slurries can not be prepared from ingredients which can be used in personal care products such as cosmetics shampoos and the like nor can be manufactured using ingredients suitable for use in indirect contact with food.

Despite the above teachings, there still exists a need in the art for liquid suspensions for water-soluble polymers that are environmentally friendly; suitable for use in personal care products, such as cosmetics and shampoos and the like; can be manufactured using ingredients suitable for use in indirect contact with food; are extremely stable over long periods of time and are operative over a wide temperature range; and are comprised of materials that are commercially available or easy to manufacture.

SUMMARY OF THE INVENTION

In accordance with the present invention, a non-aqueous suspension includes one or more water-soluble polymers, polyalkylene glycol, and a suspension stabilizer of hydrogenated castor oil or wax. The non-aqueous suspension includes from about 0.1 to about 75 percent by weight water-soluble polymer, from about 20 to about 99.8 percent by weight polyethylene glycol, and from about 0.1 to about 5 percent by weight hydrogenated castor oil or wax.

The water-soluble polymer is selected from the group consisting of guar, hydroxyalkyl guar, carboxyalkyl guar, carboxyalkyl hydroxyalkyl guar, cationic guar, hydrophobically modified guar, hydrophobically modified hydroxyalkyl guar, hydrophobically modified carboxyalkyl guar, hydrophobically modified carboxyalkyl hydroxyalkyl guar, hydrophobically modified cationic guar, pectin, alginates, locust bean gum, gum arabic, gum acacia, carrageenan, hydroxyalkyl cellulose, carboxyalkyl hydroxyalkyl cellulose, carboxyalkyl cellulose, alkyl ethers of cellulose, hydroxyalkyl methyl cellulose, hydrophobically modified hydroxyalkyl cellulose, hydrophobically modified carboxyalkyl hydroxyalkyl cellulose, hydrophobically modified carboxyalkyl cellulose, hydrophobically modified alkyl ethers of cellulose, hydrophobically modified hydroxyalkyl methyl cellulose, starch, gum tragacanth, gum karaya, tara gum, xanthan gum, welan gum, succinoglucans, polyvinyl alcohol, polyacrylates such as the Carbopol® type polyacrylamide. The water soluble polymer may further be xanthan gum, guar gum, or cationic-, hydroxyalkyl-, carboxyalkyl-, or carboxyalkylhydroxyalkyl-derivatized guar gum.

The polyalkylene glycol is selected from the group consisting of polyethylene glycol, polypropylene glycol, and mixtures thereof. The polyalkylene glycol includes a thickener selected from the group consisting of partially neutralized polyacrylic acid, hydroxypropyl cellulose, highly substituted hydroxypropyl guar, hydrated thickening silica including fumed silica and hydrophobic fumed silica, their functional equivalents, and mixtures thereof. The hydrated thickening silicas are selected from the group consisting of colloidal gel silicas and hydrophobic derivatives thereof.

The suspension further includes one or more of the following additive materials selected from the group consisting of acids, bases, buffers, surfactants, demulsifiers, non-emulsifiers, foaming agents, antifoaming agents, scale inhibitors, corrosion inhibitors, polymer preservatives, bactericides, antioxidants, fluid loss additives, water miscible co-solvents, formation clay stabilizers, crosslinkers, polymer breakers, and gel breakers.

A method of formulating a non-aqueous suspension includes dispersing from about 0.1 to 75% suspension weight of one or more water soluble polymers and from about 0.1 to 5.0% suspension weight of a hydrogenated castor oil or wax into from about 20 to 99.8% suspension weight of polyalkylene glycol. The one or more water soluble polymers, the hydrogenated castor oil or wax, and the polyalkylene glycol are agitated until the one or more water soluble polymers are uniformly dispersed in the polyalkylene glycol and the hydrogenated castor wax dissolves.

It is therefore an object of the present invention to provide suspensions for water-soluble polymers that are environmentally friendly.

It is another object of the present invention to provide suspensions suitable for use in personal care products, such as cosmetics and shampoos and the like.

It is still another object of the present invention to provide suspensions that can be manufactured using ingredients suitable for use in indirect contact with food.

It is a further object of the present invention to provide suspensions that are extremely stable over long periods of time and that are operative over a wide temperature range.

It is still a further object of the present invention to provide suspensions that are comprised of materials that are commercially available or easy to manufacture.

Still other objects, features, and advantages of the present invention will become evident to those of ordinary skill in the art in light of the following.

DETAILED DESCRIPTION OF THE PREFERRED EMBODIMENT

The first element of the liquid polymer suspension includes a water-soluble polymer. The polymers may be derived naturally from plants and optionally may then be further derivatized to impart added functionality in the desired application. A fermentation process may also produce the polymers. The polymers may also be produced synthetically.

Typically the polymer will be a polysaccharide or derivative thereof. The polymer comprises from 0.1 to about 75% of the weight of the suspension; more preferably from 30 to 60% of the weight of the suspension; most preferably from 40 to 50% of the weight of the suspension. Polymers are preferably selected from the following group: Natural polymers and derivatives thereof: guar, hydroxyalkyl guar, carboxyalkyl guar, carboxyalkyl hydroxyalkyl guar, cationic guar, hydrophobically modified guar, hydrophobically modified hydroxyalkyl guar, hydrophobically modified carboxyalkyl guar, hydrophobically modified carboxyalkyl hydroxyalkyl guar, hydrophobically modified cationic guar, pectin, alginates, locust bean gum, gum arabic, gum acacia, carrageenan, hydroxyalkyl cellulose, carboxyalkyl hydroxyalkyl cellulose, carboxyalkyl cellulose, alkyl ethers of cellulose, hydroxyalkyl methyl cellulose, hydrophobically modified hydroxyalkyl cellulose, hydrophobically modified carboxyalkyl hydroxyalkyl cellulose, hydrophobically modified carboxyalkyl cellulose, hydrophobically modified alkyl ethers of cellulose, hydrophobically modified hydroxyalkyl methyl cellulose, starch, gum tragacanth, gum karaya, tara gum; polysaccharides produced by fermentation techniques: xanthan gum, welan gum, succinoglucans; and synthetic polymers: polyvinyl alcohol, polyacrylates such as the Carbopol® type, polyacrylamide. Mixtures of the above polymers are expressly contemplated as falling within the scope of the present invention.

The second element in the suspension includes polyalkylene glycol or thickened polyalkylene glycol. The amount of this ingredient varies between about 20 to 99.8% of the weight of the suspension. Particularly preferred is the use of polyethylene glycol or polypropylene glycol. Even most preferred is the use of low molecular weight glycols having a molecular weight of less than 1000, more preferably having a molecular weight between 100 and 600 and most preferably between 200 and 500. The use of polyethylene glycol having a molecular weight of 200 can be used, for example. The use of a polyethylene or polypropylene glycol having a molecular weight of 300 or higher and manufactured in accordance with the specifications of the National Formulary can be used in cosmetic grade applications. The use of a technical grade of polyethylene or polypropylene glycol having a molecular weight of 300 or higher as indirect additives for food contact materials and the like. The use of technical grades of polyethylene glycol with a molecular weight of 300 or higher are exempt from residue tolerance when used as inert ingredients in pesticide formulations for use to growing crops.

The term "thickened polyalkylene glycol" refers to polyalkylene glycols having preferably between 0.1 and 4% thickener selected from the group consisting of partially neutralized polyacrylic acid, hydroxypropyl cellulose, highly substituted hydroxypropyl guar, hydrated thickening silica including fumed silica and hydrophobic fumed silica, or their functional equivalents or mixtures thereof. The preferred hydrated thickening silicas, also known as thickening silicas, are colloidal gel silicas or hydrophobic derivatives thereof. More preferred ones are Aerosil®200 silica, available from Degussa Corporation, Ridgefield Park N.J., and CAB-O-SIL®M-5 and TS-530 available from Cabot Corporation, Tuscola, Ill. The most preferred is CAB-O-SIL® TS-530.

The third element of the suspension includes a finely divided hydrogenated castor oil or wax. The hydrogenated castor oil or wax is present in the amount from 0.1 to 5%; more preferably in the amount of 0.3 to 3%; and most preferably in the amount of 0.5 to 2% of the weight of the suspension. Süd Chemie of Louisville, Ky. sells the preferred hydrogenated castor wax under the name of Rheocin®. Rheocin® is acceptable for use as an indirect food additive in Title 21 of the Code of Federal Regulations.

In addition to the three elements, the suspension may also contain the following optional ingredients: acids, bases, buffers, surfactants, demulsifiers, non-emulsifiers, foaming or antifoaming agents, scale and/or corrosion inhibitors, polymer preservatives, bactericides, antioxidants, fluid loss additives, water miscible co-solvents, formation clay stabilizers, crosslinkers, polymer and gel breakers, and other materials that aid the water-soluble polymer in performing its intended application and that are well-known by those of ordinary skill in the art of formulating fluids for hydraulic fracturing and related applications.

The suspensions may be used in any number of commercial applications in addition to that of well fracturing as described above, where dry water-soluble polymers have previously been used, as well as in applications where dry water-soluble polymers have not been well suited due to their slow dissolution rates. Since the suspensions are particularly useful for applications involving dispersing the water-soluble polymers in aqueous solutions, other applications where the instant invention may be useful include environmental applications (e.g., re-mediation projects), agricultural applications (e.g. anti-misting compounds for spray or aerial application of agricultural chemicals), metal working fluids, paper applications, textile applications, cosmetic or personal care applications, cleaners, detergents, aerial firefighting applications, construction products (e.g. paint, joint cements, texture finishing compounds and the like), ceramic applications, emulsion stabilizers, adhesives, and inks. Many of the kinds of additives specifically enumerated as useful with the instant invention as it may be employed in the well fracturing arts, as well as other additives that may be particular to the practice of the other applications listed above, may also have use in the other applications for the suspension as herein listed.

Specific applications of the suspensions are as follows: In the paper industry, the suspensions may be used as drainage and retention aids, in clarification of white water, as wet and dry strength resins, and as creeping aids. Ingredients of the suspensions may be selected from materials that may be used as indirect food additives for food packaging materials for aqueous and fatty foods (21CFR176.170) or dry foods (21CFR176.180).

In the textile industry, the suspensions may be used in carpet printing and dyeing, where it is imperative that the water-soluble polymer not contain lumps when coating onto the fabric as such lumps can reduce the value of the carpet from first quality to second. The suspensions may also be used as stabilizers for foamed backings for carpets. The suspensions may also be used as sizing compounds.

In the petroleum industry, polymer flooding is used to enhance recovery of oil remaining in a formation. In this application, the water-soluble polymer suspension, particularly the xanthan gum suspensions, can be used to lower the pumping friction, to raise the low shear viscosity to control fluid loss to the surrounding strata, and to push the oil to the pumping well. The polymers are also used in drilling muds, completion and work-over fluids, acidizing and fracturing fluids, in barrier fluids to control the water-oil ratio and in polymer flooding operations. The use of these polymers in flooding operations is becoming more important as the price of petroleum continues to increase and the availability continues to decrease. The use of these polymers behind a micellar fluid allows the petroleum producer to obtain a third crop of oil from the fields.

The water-soluble polymer suspension can also be used in well stimulation applications, where substantially aqueous based polymer solutions may be made by admixing the polymer suspension of this invention to water, or waters containing from about 0.01% by weight salt to about 10% by weight salt, where the salt may be either sodium or potassium chloride. The polymer suspension of the present invention may also be added to waters made acidic by the addition of from about 0.01% by weight to about 50% by weight concentrated hydrochloric acid (approximately 32° baume), so that the hydrogen chloride content of the aqueous acid solution is from about 0.01% to about 20% by weight of the total fluid weight. Polymer suspensions where the polymer is acid resistant, such as may be the case with certain bio-polymers, such as Xanthan, and synthetic polymers, such as polyacrylamides, are preferred where the polymer suspension is to be incorporated into an acid solution.

Polymer solutions made viscous by the addition of the polymer suspension of the instant invention to water, brines, or acid solutions, may be crosslinked with aluminum, boron, titanium, zirconium, combinations of these, or other metal complexes well-known to those of ordinary skill in the art of formulating fracturing fluids to make a gelled fluid suitable, with additives appropriate to particular well-treating conditions, for fracturing. The environmentally friendly and low-toxicity characteristics of the polymer suspension makes it particularly useful for fracturing in environmentally sensitive environments, such as offshore.

In the personal care industry, polymers are used as thickening and conditioning agents in hair care products such as shampoos and conditioners. They are also used as rheology control agents in toothpastes and gels. The ingredients used in formulating the water-soluble polymers can be selected from approved materials for this application.

Other uses for the polymers include those where the products are utilized as thickeners and suspending agents in aqueous emulsions, such as water-thinned paints. Still other uses include hair sprays, gelatin substitutes for photographic applications, ceramics, cleaners, polishers, inks, fire-fighting chemicals, indirect food additives, metal-working chemicals, components of adhesives and explosive formulations, binders for sand, ores, and coal.

EXAMPLES

Example 1

A method for making suspensions of water soluble polymers includes dispersing from 0.1 to 75% suspension weight of a water soluble polymer and from 0.1 to 5.0% suspension weight of a hydrogenated castor oil or wax into from 20 to 99.8% suspension weight of polyalkylene glycol. The water soluble polymer, hydrogenated castor oil or wax, and polyalkylene glycol are mixed using conventional agitation, such as an overhead mixer, until the polymer is uniformly dispersed in the polyalkylene glycol and the hydrogenated castor wax has dissolved.

Example 2 (Control)

120 grams of a finely milled high-grade guar gum are dispersed into 180 grams of polyethylene glycol (200 MW) in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents are transferred to a 100 ml graduated cylinder for subsequent measurement of the supernatant separation over time. The balance of the material is transferred to another container for evaluation of particle packing and other properties as desired.

| Composition (% by weight) | | |
|---|---|---|
| Guar gum | 40% | |
| Polyethylene glycol 200 MW | 60% | |
| Initial viscosity | 5500 cP | |
| Properties on aging | supernatant separation | Particle packing |
| 24 hours | 7% by volume | medium packed. Difficult to remix with stirring rod. |
| 3 days | 15% by volume | Hard packed, cannot remix with stirring rod. |
| 1 week | 20% by volume | Hard packed, cannot remix with stirring rod. |

Example 3

120 grams of a finely milled high grade guar gum and either 0.6 or 2% of Rheocin® are dispersed into polyethylene glycol (200 MW) making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents are transferred to a 100 ml graduated cylinder for subsequent measurement of the supernatant separation over time. The balance of the material is transferred to another container for evaluation of particle packing and other properties as desired.

| Composition (% by weight) | 2A | 2B | | |
|---|---|---|---|---|
| Guar gum | 40% | 40% | | |
| Rheocin ® | 0.6% | 2% | | |
| Polyethylene glycol 200 MW | 59.4% | 58% | | |
| Initial viscosity | 3500 | 4400 | | |
| Properties upon aging | | | | |
|  | Separation | Packing | Separation | Packing |
| 24 hours | 5% | none | 2% | none |
| 3 days | 7% | none | 2% | none |
| 1 month | 10% | difficult remix | 2.5% | none |

Example 4

120 grams of a finely milled high grade guar gum and either 0.75, 1.0 or 1.25% of Rheocin® are dispersed into polyethylene glycol (200 MW) which has been pre-thickened with a thickening silica, specifically with 1.68% CAB-O-SIL® TS-530, making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents are transferred to a 100 ml graduated cylinder for subsequent measurement of the supernatant separation over time. The balance of the material is transferred to another container for evaluation of particle packing and other properties as desired.

| Composition | 3A | | 3B | | 3C | |
|---|---|---|---|---|---|---|
| Guar Gum | 40% | | 40% | | 40% | |
| Rheocin ® | 0.75% | | 1.0% | | 1.25% | |
| Polyethylene Glycol (200) (Pre-thickened with 1.68% CAB-O-SIL ® TS-530) | 59.25% | | 59% | | 58.75% | |
| Initial Viscosity Properties on Aging | 6700 cP | | 8100 cP | | 8600 cP | |
| | Separation | Packing | Separation | Packing | Separation | Packing |
| 24 hours | 0 | none | 0 | none | 0 | none |
| 1 month | 3% | none | 1% | none | 0 | none |
| 2 months | 3% | none | 1% | none | less than 1% | none |
| 3 months | 4% | none | 2% | none | 1% | none |

All of the above compositions are easily pourable or pumpable

Example 5

4.8 grams of the sample identified as 3B above is drawn into a 5 cc syringe. This sample is rapidly injected into 395.2 grams of water contained in a 600 ml Griffin beaker under agitation. This is equal to a concentration of active guar gum of 0.48% by weight of the total solution. The water is agitated at a speed of 300 rpm with a 2.5 inch diameter 3 blade propeller by means of a precision overhead mixer for a period of 2 minutes. At this rotational speed the surface of the water has a negligible vortex. The sample rapidly disperses without lumps or fisheyes and begins to develop viscosity.

As a comparison, a conventional diesel slurry of guar is prepared by the following formula:

| | |
|---|---|
| Diesel fuel #2 | 53% |
| Tixogel MP (organically modified clay) | 1.2% |
| 95% methanol | 0.3% |
| Above mixed at high shear for 30 minutes and the following is added: | |
| Ethoxylated nonylphenol (9.5 moles E.O.) | 0.5% |
| Guar gum (of the same lot as Example 3B) | 45% |

4.27 grams of this conventional diesel slurry of guar is drawn into a 5 cc syringe. This sample is rapidly injected into 395.73 grams of water contained in a 600 ml Griffin beaker under agitation. This is equal to a concentration of active guar gum of 0.48% by weight of the total solution. The water is agitated at a speed of 300 rpm with a 2.5 inch diameter 3 blade propeller by means of a precision overhead mixer for a period of 2 minutes. At this rotational speed the surface of the water has a negligible vortex. The sample rapidly disperses without lumps or fisheyes and begins to develop viscosity.

As a further comparison, 1.92 grams of the same lot of finely milled powdered high grade guar gum is rapidly added to 398.08 grams of water and mixed using the conditions above. This is also equal to a concentration of 0.48% by weight of the total solution. The solution contains lumps and fisheyes. Listed below is a comparison of the viscosity of the aqueous viscosity as measured on a Fann 35 viscometer using a #1 spring with a R1-B1 configuration at 300 rpm.

| Time | Guar Suspension Example 3B | Conventional Diesel Slurry | Guar Powder |
|---|---|---|---|
| 5 minutes | 11 cP | 10 cP | 7 cP |
| 10 minutes | 15 cP | 14 cP | 11 cP |
| 30 minutes | 28 cP | 27 cP | 20 cP |
| 1 hour | 29 cP | 28 cP | 21 cP |
| 2 hours | 32 cP | 31 cP | 23 cP |

As can be seen from the above comparison, the guar suspension from example 3B develops viscosity upon dilution that is equivalent to the conventional diesel slurry. The formation of lumps significantly reduces the efficiency of the finely milled powdered guar gum for the purposes of thickening water.

Example 6

The aqueous dilution prepared from Example 3B as illustrated in Example 4 is analyzed for extractable oil and grease using EPA Method 413.1. 5 mg/l of extractable oil and grease are measured using this method. This compares favorably to the regulations issued by the Environmental Protection Agency that limit the amount of oil or grease that can be used in offshore oilfield applications for well treatment fluids. The National Pollutant Discharge Elimination System General Permit issued on Apr. 19, 1999 (Federal Register Vol. 64 No. 74) limits the oil and grease to a daily maximum concentration of 42 mg/l and a monthly average of 29 mg/l when the suspension is diluted to the intended use level with fresh or salt water. Non-aqueous suspensions that use a hydrocarbon such as diesel fuel, mineral oil or isopariffms as a solvent that is completely extractable as oil and grease by the above method at a concentration of 53% of the weight of the slurry will yield a theoretical concentration of 5985 mg/l oil and grease.

Example 7

The aqueous dilution prepared from Example 3B as illustrated in Example 4 is tested for the 96 hour static definitive toxicity test using mysid shrimp (*Mysidopsis bahia*) as the test organism. This is the test used to determine the toxicity of an offshore oil well treatment fluid that is to be used in the Gulf of Mexico within the jurisdiction of the United States Environmental Protection Agency. The analytical method was issued by the U.S. Environmental Protection agency in March 1993. Appendix 2 to subpart A of Part 435—Drilling Fluids Toxicity Test, Final Rule for Offshore Subcategory of the Oil and Gas Extraction Point Category, *Federal Register*/Volume 58, No.41/Thursday, Mar. 4, 1993 (40CFR Part 435/12507). The $LC_{50}$ for the dilution prepared in Example 4 exceeded 1,000,000 parts per million.

Example 8

A sample of a hydroxypropyl guar derivative suspension is prepared. 120 grams of a hydroxypropyl guar (Galactosol® 40H4FD1 sold by Aqualon Division of Hercules) and 3 grams of Rheocin® are dispersed into 177 grams of polyethylene glycol (200 MW) which has been pre-thickened with a thickening silica, specifically with 1.68% CAB-O-SIL® TS-530, making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents are transferred to a 100 ml graduated cylinder for subsequent measurement of the supernatant separation over time. The balance of the material is transferred to another container for evaluation of particle packing and other properties as desired.

| Composition | |
|---|---|
| Hydroxypropyl guar | 40% |
| Rheocin ® | 1.0% |
| Polyethylene Glycol (200) (Pre-thickened with 1.68% CAB-O-SIL ® TS-530) | 59% |

| Properties on aging | | |
|---|---|---|
| Initial Viscosity | 4900 cP | |
| Properties on Aging | Separation | Packing |
| 24 hours | 0 | none |
| 1 week | 0 | none |
| 1 month | 2% | none |

Example 9

A sample of a xanthan gum suspension is prepared. 120 grams of a xanthan gum (Kelzan XC, a product of Kelco division of Monsanto Corporation) and 3 grams of Rheocine® are dispersed into 177 grams of polyethylene glycol (200 MW) which has been pre-thickened with a thickening silica, specifically with 1.68% CAB-O-SIL® TS-530, making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents are transferred to a 100 ml graduated cylinder for subsequent measurement of the supernatant separation over time. The balance of the material is transferred to another container for evaluation of particle packing and other properties as desired.

| Composition | |
|---|---|
| Xanthan Gum | 40 |
| Rheocin ® | 1.0% |
| Polyethylene Glycol (200) (Pre-thickened with 1.68% CAB-O-SIL ® TS-530) | 59% |

| Initial Viscosity | 4900 cP | |
|---|---|---|
| Properties on Aging | Separation | Packing |
| 24 hours | 0 | none |
| 1 week | 0 | none |
| 1 month | 1% | none |

Example 10

A sample of a polyvinyl alcohol suspension is prepared. 105 grams of a polyvinyl alcohol (such as Elvanol 50-42, a product of the DuPont Corporation) and 3 grams of Rheocin® are dispersed into 192 grams of polyethylene glycol (200 MW) which has been pre-thickened with a thickening silica, specifically with 1.68% CAB-O-SIL® TS-530, making up the balance in a 600 ml beaker. The mixture is agitated using an overhead mixer at 700 rpm for a period of 1 hour. At this time the viscosity of the mixture is measured on a Brookfield RV viscometer at 20 rpm using a #4 spindle. A portion of the contents are transferred to a 100 ml graduated cylinder for subsequent measurement of the supernatant separation over time. The balance of the material is transferred to another container for evaluation of particle packing and other properties as desired.

| Composition | |
|---|---|
| Polyvinyl alcohol | 35% |
| Rheocin ® | 1.0% |
| Polyethylene Glycol (200) (Pre-thickened with 1.68% CAB-O-STL ® TS-530) | 64% |

| Properties on aging | | |
|---|---|---|
| Initial Viscosity | 2500 cP | |
| Properties on Aging | Separation | Packing |
| 24 hours | 0 | none |
| 1 month | 1% | none |
| 3 months | 1% | none |

Example 11

Samples of suspensions of guar gum were prepared using polyglycols with molecular weights higher and lower than 200. The pour point of the undiluted suspensions was tested using the ASTM Method D-97-87$^{e1}$ Standard Test Method for Pour Point of Petroleum Oils. The purpose of this experiment was to determine if other solvents could be used in the system and maintain a flowable suspension in a cold winter environment. Samples were tested for flowability at −5° F. In this case the solvent was thickened in situ with the thickening silica rather than by pre-thickening the solvent. Sodium Bicarbonate was added as a pH buffer.

| Composition | 10A | 10B | 10C |
|---|---|---|---|
| Triethylene Glycol | 57.7% | 0 | 0 |
| Polyethylene Glycol 200 | 0 | 57.7% | 0 |
| Polyethylene Glycol 300 | 0 | 0 | 57.7% |
| CAB-O-SIL ® TS-530 | 1% | 1% | 1% |
| Rheocin ® | 0.9% | 0.9% | 0.9% |
| Sodium Bicarbonate | 0.4% | 0.4% | 0.4% |
| Flowable at −5° F. | Yes | Yes | No |

Although the present invention has been described in terms of the foregoing embodiment, such description has been for exemplary purposes only and, as will be apparent to one of ordinary skill in the art, many alternatives, equivalents, and variations of varying degrees will fall within the scope of the present invention. That scope, accordingly, is not to be limited in any respect by the foregoing description; rather, it is defined only by the claims that follow.

I claim:

1. A non-aqueous suspension, comprising:
   (a) polyalkylene glycol;
   (b) one or more water-soluble polymers dispersed in the polyalkylene glycol; and
   (c) a suspension stabilizer comprising an hydrogenated castor oil or wax.

2. The suspension according to claim 1 wherein the water-soluble polymer is selected from the group consisting of guar, hydroxyalkyl guar, carboxyalkyl guar, carboxyalkyl hydroxyalkyl guar, cationic guar, hydrophobically modified guar, hydrophobically modified hydroxyalkyl guar, hydrophobically modified carboxyalkyl guar, hydrophobically modified carboxyalkyl hydroxyalkyl guar, hydrophobically modified cationic guar, pectin, alginates, locust bean gum, gum arabic, gum acacia, carrageenan, hydroxyalkyl cellulose, carboxyalkyl hydroxyalkyl cellulose, carboxyalkyl cellulose, alkyl ethers of cellulose, hydroxyalkyl methyl cellulose, hydrophobically modified hydroxyalkyl cellulose, hydrophobically modified carboxyalkyl hydroxyalkyl cellulose, hydrophobically modified carboxyalkyl cellulose, hydrophobically modified alkyl ethers of cellulose, hydrophobically modified hydroxyalkyl methyl cellulose, starch, gum tragacanth, gum karaya, tara gum, xanthan gum, welan gum, succinoglucans, polyvinyl alcohol, polyacrylates, and polyacrylamides.

3. The suspension according to claim 1 wherein the water-soluble polymer is xanthan gum.

4. The suspension according to claim 1 wherein the water-soluble polymer is guar gum.

5. The suspension according to claim 1 wherein the water-soluble polymer is cationic-, hydroxyalkyl-, carboxyalkyl-, or carboxyalkylhydroxyalkyl-derivatized guar gum.

6. The suspension according to claim 1 wherein the polyalkylene glycol is selected from the group consisting of polyethylene glycol, polypropylene glycol, and mixtures thereof.

7. The suspension according to claim 1 wherein the polyalkylene glycol includes a thickener selected from the group consisting of partially neutralized polyacrylic acid, hydroxypropyl cellulose, highly substituted hydroxypropyl guar, hydrated thickening silicas.

8. The suspension according to claim 7 wherein the hydrated thickening silicas are selected from the group consisting of colloidal gel silicas and hydrophobic derivatives thereof.

9. The suspension according to claim 1 wherein the polyalkylene glycol has a molecular weight of less than 1000.

10. The suspension according to claim 1 further comprising one or more of the following additive materials selected from the group consisting of acids, bases, buffers, surfactants, demulsifiers, non-emulsifiers, foaming agents, antifoaming agents, scale inhibitors, corrosion inhibitors, polymer preservatives, bactericides, antioxidants, fluid loss additives, water miscible co-solvents, formation clay stabilizers, crosslinkers, polymer breakers, and gel breakers.

11. A non-aqueous suspension, comprising:
    (a) about 0.1 to about 75 percent by weight water-soluble polymer;
    (b) about 20 to about 99.8 percent by weight polyethylene glycol; and
    (c) about 0.1 to about 5 percent by weight hydrogenated castor oil or wax.

12. The suspension according to claim 11 wherein the water-soluble polymer is selected from the group consisting of guar, hydroxyalkyl guar, carboxyalkyl guar, carboxyalkyl hydroxyalkyl guar, cationic guar, hydrophobically modified guar, hydrophobically modified hydroxyalkyl guar, hydrophobically modified carboxyalkyl guar, hydrophobically modified carboxyalkyl hydroxyalkyl guar, hydrophobically modified cationic guar, pectin, alginates, locust bean gum, gum arabic, gum acacia, carrageenan, hydroxyalkyl cellulose, carboxyalkyl hydroxyalkyl cellulose, carboxyalkyl cellulose, alkyl ethers of cellulose, hydroxyalkyl methyl cellulose, hydrophobically modified hydroxyalkyl cellulose, hydrophobically modified carboxyalkyl hydroxyalkyl cellulose, hydrophobically modified carboxyalkyl cellulose, hydrophobically modified alkyl ethers of cellulose, hydrophobically modified hydroxyalkyl methyl cellulose, starch, gum tragacanth, gum karaya, tara gum, xanthan gum, welan gum, succinoglucans, polyvinyl alcohol, polyacrylates, and polyacrylamides.

13. The suspension according to claim 11 wherein the water-soluble polymer is xanthan gum.

14. The suspension according to claim 11 wherein the water-soluble polymer is guar gum.

15. The suspension according to claim 11 wherein the water-soluble polymer is cationic-, hydroxyalkyl-, carboxyalkyl-, or carboxyalkylhydroxyalkyl-derivatized guar gum.

16. The suspension according to claim 11 wherein the polyalkylene glycol is selected from the group consisting of polyethylene glycol, polypropylene glycol, and mixtures thereof.

17. The suspension according to claim 11 wherein the polyalkylene glycol further comprises between about 0.1 and 2.0% by weight of the polyalkylene glycol of a thickener selected from the group consisting of partially neutralized polyacrylic acid, hydroxypropyl cellulose, highly substituted hydroxypropyl guar, hydrated thickening silicas.

18. The suspension according to claim 17 wherein the hydrated thickening silicas are selected from the group consisting of colloidal gel silicas and hydrophobic derivatives thereof.

19. The suspension according to claim 11 wherein the polyalkylene glycol has a molecular weight of less than 1000.

20. The suspension according to claim 11 further comprising one or more of the following additive materials selected from the group consisting of acids, bases, buffers, surfactants, demulsifiers, non-emulsifiers, foaming agents, antifoaming agents, scale inhibitors, corrosion inhibitors, polymer preservatives, bactericides, antioxidants, fluid loss additives, water miscible co-solvents, formation clay stabilizers, crosslinkers, polymer breakers, and gel breakers.

21. A non-aqueous suspension, comprising:
    (a) about 0.1 to about 40.0 percent by weight xanthan gum;
    (b) about 55 to about 99.8 percent by weight polyethylene glycol; and
    (c) about 0.1 to about 5 percent by weight hydrogenated castor wax.

22. The suspension according to claim 21 wherein the polyalkylene glycol is selected from the group consisting of polyethylene glycol, polypropylene glycol, and mixtures thereof.

23. The suspension according to claim 21 wherein the polyalkylene glycol further comprises between about 0.1 and 2.0% by weight of the polyalkylene glycol of a thickener selected from the group consisting of partially neutralized polyacrylic acid, hydroxypropyl cellulose, highly substituted hydroxypropyl guar, hydrated thickening silicas.

24. The suspension according to claim 23 wherein the hydrated thickening silicas are selected from the group consisting of colloidal gel silicas and hydrophobic derivatives thereof.

25. The suspension according to claim 21 wherein the polyalkylene glycol has a molecular weight of less than 1000.

26. The suspension according to claim 21 further comprising one or more of the following additive materials selected from the group consisting of acids, bases, buffers, surfactants, demulsifiers, non-emulsifiers, foaming agents, antifoaming agents, scale inhibitors, corrosion inhibitors, polymer preservatives, bactericides, antioxidants, fluid loss additives, water miscible co-solvents, formation clay stabilizers, crosslinkers, polymer breakers, and gel breakers.

27. A non-aqueous suspension, comprising:
(a) about 0.1 to about 75 percent by weight guar gum;
(b) about 55 to about 99.8 percent by weight polyethylene glycol; and
(c) about 0.1 to about 5 percent by weight hydrogenated castor wax.

28. The suspension according to claim 27 wherein the polyalkylene glycol is selected from the group consisting of polyethylene glycol, polypropylene glycol, and mixtures thereof.

29. The suspension according to claim 27 wherein the polyalkylene glycol further comprises between about 0.1 and 2.0% by weight of the polyalkylene glycol of a thickener selected from the group consisting of partially neutralized polyacrylic acid, hydroxypropyl cellulose, highly substituted hydroxypropyl guar, and hydrated thickening silicas.

30. The suspension according to claim 29 wherein the hydrated thickening silicas are selected from the group consisting of colloidal gel silicas and hydrophobic derivatives thereof.

31. The suspension according to claim 27 wherein the polyalkylene glycol has a molecular weight of less than 1000.

32. The suspension according to claim 27 further comprising one or more of the following additive materials selected from the group consisting of acids, bases, buffers, surfactants, demulsifiers, non-emulsifiers, foaming agents, antifoaming agents, scale inhibitors, corrosion inhibitors, polymer preservatives, bactericides, antioxidants, fluid loss additives, water miscible co-solvents, formation clay stabilizers, crosslinkers, polymer breakers, and gel breakers.

33. A non-aqueous suspension, comprising:
(a) about 0.1 to about 50 percent by weight cationic-, hydroxyalkyl-, carboxyalkyl-, or carboxyalkylhydroxyalkyl-derivatized guar gum;
(b) about 55 to about 99.8 percent by weight polyethylene glycol; and
(c) about 0.1 to about 5 percent by weight hydrogenated castor wax.

34. The suspension according to claim 33 wherein the polyalkylene glycol is selected from the group consisting of polyethylene glycol, polypropylene glycol, and mixtures thereof.

35. The suspension according to claim 33 wherein the polyalkylene glycol further comprises between about 0.1 and 2.0% by weight of the polyalkylene glycol of a thickener selected from the group consisting of partially neutralized polyacrylic acid, hydroxypropyl cellulose, highly substituted hydroxypropyl guar, and hydrated thickening silica.

36. The suspension according to claim 35 wherein the hydrated thickening silicas are selected from the group consisting of colloidal gel silicas and hydrophobic derivatives thereof.

37. The suspension according to claim 33 wherein the polyalkylene glycol has a molecular weight of less than 1000.

38. The suspension according to claim 33 further comprising one or more of the following additive materials selected from the group consisting of acids, bases, buffers, surfactants, demulsifiers, non-emulsifiers, foaming agents, antifoaming agents, scale inhibitors, corrosion inhibitors, polymer preservatives, bactericides, antioxidants, fluid loss additives, water miscible co-solvents, formation clay stabilizers, crosslinkers, polymer breakers, and gel breakers.

39. A composition comprising environmental chemical, agricultural chemical, paper chemical, textile chemical, construction or building product ingredient, cosmetic ingredients, hair spray, gelatin substitute, ceramic material, cleaning composition, polish, ink, fire-fighting chemical, metal-working chemical, adhesive chemical, explosive chemical, flocculent, water treatment compound, binder chemical for sand, ores or coal or oil field chemical which includes a non-aqueous suspension, comprising:
(a) polyalkylene glycol;
(b) one or more water-soluble polymers dispersed in the polyalkylene glycol; and
(c) a suspension stabilizer comprising an hydrogenated castor oil or wax.

40. The composition according to claim 39 wherein the water-soluble polymer is selected from the group consisting of guar, hydroxyalkyl guar, carboxyalkyl guar, carboxyalkyl hydroxyalkyl guar, cationic guar, hydrophobically modified guar, hydrophobically modified hydroxyalkyl guar, hydrophobically modified carboxyalkyl guar, hydrophobically modified carboxyalkyl hydroxyalkyl guar, hydrophobically modified cationic guar, pectin, alginates, locust bean gum, gum arabic, gum acacia, carrageenan, hydroxyalkyl cellulose, carboxyalkyl hydroxyalkyl cellulose, carboxyalkyl cellulose, alkyl ethers of cellulose, hydroxyalkyl methyl cellulose, hydrophobically modified hydroxyalkyl cellulose, hydrophobically modified carboxyalkyl hydroxyalkyl cellulose, hydrophobically modified carboxyalkyl cellulose, hydrophobically modified alkyl ethers of cellulose, hydrophobically modified hydroxyalkyl methyl cellulose, starch, gum tragacanth, gum karaya, tara gum, xanthan gum, welan gum, succinoglucans, polyvinyl alcohol, polyacrylates and polyacrylamides.

41. The composition according to claim 39 wherein the water-soluble polymer is xanthan gum.

42. The composition according to claim 39 wherein the water-soluble polymer is guar gum.

43. The composition according to claim 39 wherein the water-soluble polymer is cationic-, hydroxyalkyl-, carboxyalkyl-, or carboxyalkylhydroxyalkyl-derivatized guar gum.

44. The composition according to claim 39 wherein the polyalkylene glycol is selected from the group consisting of polyethylene glycol, polypropylene glycol, and mixtures thereof.

45. The composition according to claim 39 wherein the polyalkylene glycol includes a thickener selected from the group consisting of partially neutralized polyacrylic acid, hydroxypropyl cellulose, highly substituted hydroxypropyl guar, and hydrated thickening silicas.

46. The composition according to claim 45 wherein the hydrated thickening silicas are selected from the group consisting of colloidal gel silicas and hydrophobic derivatives thereof.

47. The suspension according to claim 39 wherein the polyalkylene glycol has a molecular weight of less than 1000.

48. The composition according to claim 39 further comprising one or more of the following additive materials selected from the group consisting of acids, bases, buffers, surfactants, demulsifiers, non-emulsifiers, foaming agents, antifoaming agents, scale inhibitors, corrosion inhibitors, polymer preservatives, bactericides, antioxidants, fluid loss additives, water miscible co-solvents, formation clay stabilizers, crosslinkers, polymer breakers, and gel breakers.

49. A composition of a polymer solution or dispersion comprising:
   (a) non-aqueous suspension from about 0.001 to about 10 percent by weight of the total weight, the non-aqueous suspension, comprising:
      (i) one or more water-soluble polymers,
      (ii) polyalkylene glycol, and
      (iii) a suspension stabilizer comprising an hydrogenated castor oil or wax; and
   (b) water from about 90 to about 99.999 percent by weight of the total weight.

50. The composition of claim 49 wherein the non-aqueous suspension comprises from about 0.25% by weight to about 5% by weight of the polymer solution and water comprises the balance.

51. The composition of claim 49 wherein the polymer solution or dispersion is hydrated and subsequently crosslinked to form a gel with an aluminum, antimony, boron, titanium, or zirconium compound, complex, or chelate, or some combination aluminum, antimony, boron, titanium, and zirconium compounds, complexes, or chelates.

52. The composition of claim 49 wherein one or more of the following additive materials selected from the group consisting of acids, bases, buffers, surfactants, demulsifiers, non-emulsifiers, foaming agents, antifoaming agents, scale inhibitors, corrosion inhibitors, polymer preservatives, bactericides, antioxidants, fluid loss additives, water miscible co-solvents, formation clay stabilizers, crosslinkers, polymer breakers, and gel breakers are incorporated into the hydrated polymer solution or dispersion.

53. The composition of claim 49 wherein the water is seawater, or a solution of sodium chloride, potassium chloride, or ammonium chloride, or a mixture thereof, in water.

54. The composition of claim 49 wherein the non-aqueous suspension comprises:
   (a) about 0.1 to about 75 percent by weight water-soluble polymer;
   (b) about 20 to about 99.8 percent by weight polyethylene glycol; and
   (c) about 0.1 to about 5 percent by weight hydrogenated castor oil or wax.

55. The suspension according to claim 54 wherein the polyalkylene glycol further comprises between about 0.1 and 2.0% by weight of the polyalkylene glycol of a thickener selected from the group consisting of partially neutralized polyacrylic acid, hydroxypropyl cellulose, highly substituted hydroxypropyl guar, and hydrated thickening silicas.

56. The composition according to claim 49 wherein the water-soluble polymer is selected from the group consisting of guar, hydroxyalkyl guar, carboxyalkyl guar, carboxyalkyl hydroxyalkyl guar, cationic guar, hydrophobically modified guar, hydrophobically modified hydroxyalkyl guar, hydrophobically modified carboxyalkyl guar, hydrophobically modified carboxyalkyl hydroxyalkyl guar, hydrophobically modified cationic guar, pectin, alginates, locust bean gum, gum arabic, gum acacia, carrageenan, hydroxyalkyl cellulose, carboxyalkyl hydroxyalkyl cellulose, carboxyalkyl cellulose, alkyl ethers of cellulose, hydroxyalkyl methyl cellulose, hydrophobically modified hydroxyalkyl cellulose, hydrophobically modified carboxyalkyl hydroxyalkyl cellulose, hydrophobically modified carboxyalkyl cellulose, hydrophobically modified alkyl ethers of cellulose, hydrophobically modified hydroxyalkyl methyl cellulose, starch, gum tragacanth, gum karaya, tara gum, xanthan gum, welan gum, succinoglucans, polyvinyl alcohol, polyacrylates, and polyacrylamides.

57. The composition according to claim 49 wherein the water-soluble polymer is xanthan gum.

58. The composition according to claim 49 wherein the water-soluble polymer is guar gum.

59. The composition according to claim 49 wherein the water-soluble polymer is cationic-, hydroxyalkyl-, carboxyalkyl-, or carboxyalkylhydroxyalkyl-derivatized guar gum.

60. The composition according to claim 49 wherein the polyalkylene glycol is selected from the group consisting of polyethylene glycol, polypropylene glycol, and mixtures thereof.

61. The composition according to claim 49 wherein the polyalkylene glycol includes a thickener selected from the group consisting of partially neutralized polyacrylic acid, hydroxypropyl cellulose, highly substituted hydroxypropyl guar, hydrated thickening silicas.

62. The composition according to claim 61 wherein the hydrated thickening silicas are selected from the group consisting of colloidal gel silicas and hydrophobic derivatives thereof.

63. The composition according to claim 49 wherein the polyalkylene glycol has a molecular weight of less than 1000.

64. A composition of a polymer solution or dispersion comprising environmental chemical, agricultural chemical, paper chemical, textile chemical, construction or building product ingredient, cosmetic ingredients, hair spray, gelatin substitute, ceramic material, cleaning composition, polish, ink, fire-fighting chemical, metal-working chemical, adhesive chemical, explosive chemical, flocculent, water treatment compound, binder chemical for sand, ores or coal or oil field chemical which includes a non-aqueous suspension, comprising:
   (a) non-aqueous suspension from about 0.001 to about 10 percent by weight of the total weight, the non-aqueous suspension, comprising:
      (i) one or more water-soluble polymers,
      (ii) polyalkylene glycol, and
      (iii) a suspension stabilizer comprising an hydrogenated castor oil or wax; and
   (b) water from about 90 to about 99.999 percent by weight of the total weight.

65. The composition of claim 64 wherein the non-aqueous suspension comprises:
   (a) about 0.1 to about 75 percent by weight water-soluble polymer;
   (b) about 20 to about 99.8 percent by weight polyethylene glycol; and
   (c) about 0.1 to about 5 percent by weight hydrogenated castor oil or wax.

66. The composition according to claim 65 wherein the polyalkylene glycol further comprises between about 0.1 and 2.0% by weight of the polyalkylene glycol of a thickener selected from the group consisting of partially neutralized polyacrylic acid, hydroxypropyl cellulose, highly substituted hydroxypropyl guar, and hydrated thickening silicas.

67. The composition according to claim 64 wherein the water-soluble polymer is selected from the group consisting of guar, hydroxyalkyl guar, carboxyalkyl guar, carboxyalkyl hydroxyalkyl guar, cationic guar, hydrophobically modified guar, hydrophobically modified hydroxyalkyl guar, hydrophobically modified carboxyalkyl guar, hydrophobically modified carboxyalkyl hydroxyalkyl guar, hydrophobically modified cationic guar, pectin, alginates, locust bean gum, gum arabic, gum acacia, carrageenan, hydroxyalkyl cellulose, carboxyalkyl hydroxyalkyl cellulose, carboxyalkyl cellulose, alkyl ethers of cellulose, hydroxyalkyl methyl cellulose, hydrophobically modified hydroxyalkyl cellulose, hydrophobically modified carboxyalkyl hydroxyalkyl cellulose, hydrophobically modified carboxyalkyl cellulose, hydrophobically modified alkyl ethers of cellulose, hydrophobically modified hydroxyalkyl methyl cellulose, starch, gum tragacanth, gum karaya, tara gum, xanthan gum, welan gum, succinoglucans, polyvinyl alcohol, polyacrylates, and polyacrylamides.

68. The composition according to claim 64 wherein the water-soluble polymer is xanthan gum.

69. The composition according to claim 65 wherein the water-soluble polymer is guar gum.

70. The composition according to claim 65 wherein the water-soluble polymer is cationic-, hydroxyalkyl-, carboxyalkyl-, or carboxyalkylhydroxyalkyl-derivatized guar gum.

71. The composition according to claim 64 wherein the polyalkylene glycol is selected from the group consisting of polyethylene glycol, polypropylene glycol, and mixtures thereof.

72. The composition according to claim 64 wherein the polyalkylene glycol includes a thickener selected from the group consisting of partially neutralized polyacrylic acid, hydroxypropyl cellulose, highly substituted hydroxypropyl guar, and hydrated thickening silicas.

73. The composition according to claim 72 wherein the hydrated thickening silicas are selected from the group consisting of colloidal gel silicas and hydrophobic derivatives thereof.

74. The composition according to claim 64 wherein the polyalkylene glycol has a molecular weight of less than 1000.

75. The composition according to claim 64 further comprising one or more of the following additive materials selected from the group consisting of acids, bases, buffers, surfactants, demulsifiers, non-emulsifiers, foaming agents, antifoaming agents, scale inhibitors, corrosion inhibitors, polymer preservatives, bactericides, antioxidants, fluid loss additives, water miscible co-solvents, formation clay stabilizers, crosslinkers, polymer breakers, and gel breakers.

76. A method of formulating a non-aqueous suspension, comprising:
dispersing one or more water soluble polymers and a hydrogenated castor oil or wax into polyalkylene glycol; and
agitating the one or more water soluble polymers, the hydrogenated castor oil or wax, and the polyalkylene glycol until the one or more water soluble polymers are uniformly dispersed in the polyalkylene glycol and the hydrogenated castor wax dissolves.

77. The method according to claim 76 wherein the water soluble polymer is selected from the group consisting of guar, hydroxyalkyl guar, carboxyalkyl guar, carboxyalkyl hydroxyalkyl guar, cationic guar, hydrophobically modified guar, hydrophobically modified hydroxyalkyl guar, hydrophobically modified carboxyalkyl guar, hydrophobically modified carboxyalkyl hydroxyalkyl guar, hydrophobically modified cationic guar, pectin, alginates, locust bean gum, gum arabic, gum acacia, carrageenan, hydroxyalkyl cellulose, carboxyalkyl hydroxyalkyl cellulose, carboxyalkyl cellulose, alkyl ethers of cellulose, hydroxyalkyl methyl cellulose, hydrophobically modified hydroxyalkyl cellulose, hydrophobically modified carboxyalkyl hydroxyalkyl cellulose, hydrophobically modified carboxyalkyl cellulose, hydrophobically modified alkyl ethers of cellulose, hydrophobically modified hydroxyalkyl methyl cellulose, starch, gum tragacanth, gum karaya, tara gum, xanthan gum, welan gum, succinoglucans, polyvinyl alcohol, polyacrylates, and polyacrylamides.

78. The method according to claim 76 wherein the water-soluble polymer is xanthan gum.

79. The method according to claim 76 wherein the water-soluble polymer is guar gum.

80. The method according to claim 76 wherein the water-soluble polymer is cationic-, hydroxyalkyl-, carboxyalkyl-, or carboxyalkylhydroxyalkyl-derivatized guar gum.

81. The method according to claim 76 wherein the polyalkylene glycol is selected from the group consisting of polyethylene glycol, polypropylene glycol, and mixtures thereof.

82. The method according to claim 76 wherein the polyalkylene glycol includes a thickener selected from the group consisting of partially neutralized polyacrylic acid, hydroxypropyl cellulose, highly substituted hydroxypropyl guar, hydrated thickening silicas.

83. The method according to claim 82 wherein the hydrated thickening silicas are selected from the group consisting of colloidal gel silicas and hydrophobic derivatives thereof.

84. The method according to claim 76 wherein the polyalkylene glycol has a molecular weight of less than 1000.

85. The method according to claim 76 further comprising the step of dispersing one or more of the following additive materials selected from the group consisting of acids, bases, buffers, surfactants, demulsifiers, non-emulsifiers, foaming agents, antifoaming agents, scale inhibitors, corrosion inhibitors, polymer preservatives, bactericides, antioxidants, fluid loss additives, water miscible co-solvents, formation clay stabilizers, crosslinkers, polymer breakers, and gel breakers.

86. A method of formulating a non-aqueous suspension, comprising:
dispersing from about 0.1 to 75% suspension weight of one or more water soluble polymers and from about 0.1 to 5.0% suspension weight of a hydrogenated castor oil or wax into from about 20 to 99.8% suspension weight of polyalkylene glycol; and
agitating the one or more water soluble polymers, the hydrogenated castor oil or wax, and the polyalkylene glycol until the one or more water soluble polymers are uniformly dispersed in the polyalkylene glycol and the hydrogenated castor wax dissolves.

87. The method according to claim 86 wherein the water soluble polymer is selected from the group consisting of guar, hydroxyalkyl guar, carboxyalkyl guar, carboxyalkyl hydroxyalkyl guar, cationic guar, hydrophobically modified guar, hydrophobically modified hydroxyalkyl guar, hydrophobically modified carboxyalkyl guar, hydrophobically modified carboxyalkyl hydroxyalkyl guar, hydrophobically modified cationic guar, pectin, alginates, locust bean gum, gum arabic, gum acacia, carrageenan, hydroxyalkyl cellulose, carboxyalkyl hydroxyalkyl cellulose, carboxyalkyl cellulose, alkyl ethers of cellulose, hydroxyalkyl methyl cellulose, hydrophobically modified hydroxyalkyl cellulose, hydrophobically modified carboxyalkyl hydroxyalkyl cellulose, hydrophobically modified carboxyalkyl cellulose, hydrophobically modified alkyl ethers of cellulose, hydrophobically modified hydroxyalkyl methyl cellulose, starch, gum tragacanth, gum karaya, tara gum, xanthan gum, welan gum, succinoglucans, polyvinyl alcohol, polyacrylates, and polyacrylamides.

88. The method according to claim 86 wherein the water-soluble polymer is xanthan gum.

89. The method according to claim 86 wherein the water-soluble polymer is guar gum.

90. The method according to claim 86 wherein the water-soluble polymer is cationic-, hydroxyalkyl-, carboxyalkyl-, or carboxyalkylhydroxyalkyl-derivatized guar gum.

91. The method according to claim 86 wherein the polyalkylene glycol is selected from the group consisting of polyethylene glycol, polypropylene glycol, and mixtures thereof.

92. The method according to claim 86 wherein the polyalkylene glycol further comprises between about 0.1 and 2.0% by weight of the polyalkylene glycol of a thickener selected from the group consisting of partially neutralized polyacrylic acid, hydroxypropyl cellulose, highly substituted hydroxypropyl guar, hydrated thickening silicas.

93. The method according to claim 92 wherein the hydrated thickening silicas are selected from the group consisting of colloidal gel silicas and hydrophobic derivatives thereof.

94. The method according to claim 86 wherein the polyalkylene glycol has a molecular weight of less than 1000.

95. The method according to claim 86 further comprising the step of dispersing one or more of the following additive materials selected from the group consisting of acids, bases, buffers, surfactants, demulsifiers, non-emulsifiers, foaming agents, antifoaming agents, scale inhibitors, corrosion inhibitors, polymer preservatives, bactericides, antioxidants, fluid loss additives, water miscible co-solvents, formation clay stabilizers, crosslinkers, polymer breakers, and gel breakers.

96. A method of drilling and completing a well, treating a subterranean formation, or displacing hydrocarbons in a hydrocarbon bearing formation with a fluid comprising the steps of:

(a) preparing a non-aqueous suspension, comprising:
   (i) one or more water-soluble polymers,
   (ii) polyalkylene glycol, and
   (iii) a suspension stabilizer comprising an hydrogenated castor oil or wax;

(b) dispersing the non-aqueous suspension in water, thereby forming a fluid; and (c) introducing the fluid into the well or subterranean formation.

97. The method according to claim 96 wherein the non-aqueous suspension comprises from about 0.001 to about 10 percent by weight of the total fluid weight.

98. The method according to claim 96 wherein the water comprises from about 90 to about 99.999 percent by weight of the total fluid weight.

* * * * *